United States Patent [19]

Marquis

[11] 3,971,829

[45] July 27, 1976

[54] PREPARATION OF METHYLENE-BRIDGED POLYPHENYLPOLYAMINE MIXTURES

[75] Inventor: Edward Thomas Marquis, Austin, Tex.

[73] Assignee: Jefferson Chemical Company, Inc., Houston, Tex.

[22] Filed: Nov. 18, 1974

[21] Appl. No.: 524,568

[52] U.S. Cl. .................... 260/570 D; 260/453 AM; 260/570.5 P
[51] Int. Cl.² ........................................ C07C 85/08
[58] Field of Search .............................. 260/570 D

[56] References Cited
UNITED STATES PATENTS 3,860,637   1/1975   Bentley ............................. 260/570

FOREIGN PATENTS OR APPLICATIONS 1,228,495   4/1971   United Kingdom ................. 260/570

*Primary Examiner*—Robert V. Hines
*Attorney, Agent, or Firm*—James L. Bailey; Lee G. Meyer

[57] ABSTRACT

An improved process for the preparation of methylene-bridged polyphenylpolyamine mixtures having increased 4,4'-isomer content in the diaminodiphenylmethane portion by the catalyzed condensation reaction of aniline and formaldehyde is disclosed. Aniline and formaldehyde are mixed and reacted at an elevated temperature in the presence of up to about 3 weight percent of a co-catalyst system comprising about 0.1 to less than about 3.0 weight percent silica-alumina catalyst and from about 0.1 to less than about 3.0 weight percent oxalic acid, basis weight of aniline present. The novel process provides a resulting reaction product that can be easily filtered to remove the solid silica-alumina catalyst therefrom and a reaction product mixture of methylene-bridged polyphenylpolyamine mixtures having an increased 4,4'-isomer content in the diaminodiphenylmethane portion than heretofore obtained utilizing silica-alumina catalysts alone. Methylene-bridged polyphenylpolyamines are useful as epoxy curing agents, urethane cross linkers, as precursors for the preparation of corresponding methylene-bridged polyphenylpolyisocyanates, and the like.

10 Claims, No Drawings

PREPARATION OF METHYLENE-BRIDGED POLYPHENYLPOLYAMINE MIXTURES

CROSS REFERENCE TO RELATED APPLICATION

This application is related to my co-pending application entitled "Preparation of Methylene-Bridged Polyarylpolyamine mixtures," Ser. No. 524,569, filed of even date herewith which teaches the condensation of an aromatic primary amine and formaldehyde in the presence of a catalytic amount of oxalic acid.

BACKGROUND OF THE INVENTION

1. Field of Invention

This invention relates to the preparation of aromatic amines and more particularly pertains to an improved process for the preparation of polymethylene polyphenylpolyamine mixtures by the catalyzed condensation reaction of aniline and formaldehyde.

2. Description of the Prior Art

Known processes for preparing methylene-bridged polyphenylpolyamines by the catalyzed condensation reaction of aniline and formaldehyde at elevated temperatures are amply described in the literature and many patents, for example U.S. Pat. Nos. 2,683,730; 2,950,263; 3,012,008; 3,344,162; 3,362,979; 3,277,173; and 3,496,229. Generally speaking, known procedures for preparing polymethylene polyphenylpolyamine mixtures include mixing and reacting aniline and formaldehyde at elevated temperatures in the presence of an acidcontaining material as a catalyst for the reaction. The resulting polymethylene polyphenylpolyamine reaction product mixture contains a diamine portion, i.e., diaminodiphenylmethane, and higher functionality, higher molecular weight methylene-bridged polyphenylpolyamines. The diamine portion of the reaction product mixture can be substantially controlled by varying several of the reaction condition variables, such as the molar ratio of aniline to formaldehyde employed. Moreover, as known, the positional isomer content of the diamine portion of the polyphenylpolyamine reaction product, namely the 2,2'-, 2,4'-, and 4,4'-diaminodiphenylmethane isomers can be varied by varying reaction conditions and employing certain types of acidic material-containing catalysts.

For example, known processes employing strong mineral acids, such as hydrochloric acid, usually result in a polyamine reaction product mixture having high 4,4'- positional isomer content in the diamine portion. Such polyamine reaction product mixtures are particularly useful as precursors for the preparation of corresponding polyisocyanate mixtures employed in the production of certain types of elastomers, coatings, structural materials, etc.

As another example, known procedures employing solid acidic siliceous catalysts, such as silica-alumina cracking catalyst, result in the production of polyamine reaction products having diamine portions which contain higher levels of 2,2'-, and 2,4'-isomers and less 4,4'-isomer, based upon the diamine portion, than the aforementioned mineral catalyzed procedures. These polyamine reaction product mixtures are also useful as precursers for preparation of corresponding polyisocyanate mixtures which are particularly useful in the production of certain types of coatings, elastomers, and the like.

The aforementioned conventional procedures for preparing methylene-bridged polyphenylpolyamine mixtures by the acid-catalyzed condensation reaction of aniline and formaldehyde, however, suffer from several disadvantages. Strong mineral acids such as hydrochloric acid, are hgihly corrosive and procedures employing same require the use of special corrosion resistant equipment. Moreover, the employment of mineral acids generally requires neutralization of the crude condensation reaction product mixture with a basic material such as caustic to produce the desired polymethylene polyphenylpolyamine mixtures. Neutralization brings on the additional difficulties of by-product salt removal and disposal.

Conventional procedures employing solid-acidic siliceous catalysts such as silica-alumina do not suffer from corrosiveness problems and neutralization of the crude condensation reaction product is not necessary. Yet solid acidic siliceous catalyst procedures suffer from other disadvantages such as slow condensation reaction rates. In order to increase the reaction rates these catalysts, particularly silica-alumina, are employed in solid very finely powdered form in amounts of aout 3.0 weight percent, basis aniline present. However, such use has brought on the attendant difficulty of separating these solid, powdered catalysts from the crude condensation reaction product mixtures. In addition, it has been very difficult to prepare polymethylene polyphenylpolyamine mixtures containing a diamine portion having a high 4,4'- positional isomer content by such procedures. The resulting polymethylene polyphenylpolyamine mixtures must be subjected to extensive distillation procedures so as to obtain such mixtures having high 4,4'- isomer containing diamine portions.

I have now discovered a process for preparing methylene-bridged polyphenylpolyamine mixtures by the catalyzed condensation reaction of aniline and formaldehyde at elevated temperatures which does not suffer from any of the aforementioned disadvantages. Moreover, the process of my invention results in the production of a methylene-bridged polyphenylpolyamine mixture having a diamine portion containing high levels of the 4,4'positional isomer which is highly useful in the preparation of epoxy curing agents and urethane crosslinkers and as precursors for preparing corresponding polymethylene polyphenylpolyisocyanate mixtures which can be used to produce certain types of coatings, elastomers, rigid and flexible foams, and the like. The invention is based upon the discovery of a novel cocatalyst system for the aniline-formaldehyde condensation reaction.

SUMMARY OF THE INVENTION

The present invention is an improved process for the preparation of methylene-bridged polyphenylpolyamine mixtures having increased 4,4'- isomer content in the methylene diphenylamine portion by the catalytic condensation reaction of aniline and formalydehyde. The process of the invention comprises mixing and reacting aniline and formaldehyde in the presence of up to about 3 weight percent of a cocatalyst system comprising from about 0.1 to less than about 3.0 weight percent silica-alumina catalyst and from about 0.1 to less than about 3.0 weight percent oxalic acid, based upon the weight of aniline present, at a temperature of from about 150° to about 250°C. at a pressure of from about atmospheric to about 300 psig, and then recovering the mixture of methylene-bridged polyphenylpolyamines. The process of the invention provides the production of methylene-bridged polyphenylpolyamine mixtures having increased 4,4'- isomer content in the diaminodiphenylmethane portion than heretofore obtained through the employment of solid acidic siliceous catalysts, particularly the silica-alumina cracking catalyst. Moreover, recovery of the desired methylene-briged polyphenylpolyamine mixture from the crude reaction product mixture is greatly simplified by use of the co-catalyst system of the inventive process. There are no requirements to employ a neutralization-with-caustic step with the attendant desired product separation and by-product disposal problems heretofore necessary with mineral acid-catalyzed condensation reaction procedures. Furthermore, the process of the invention allows the utilization of substantially less silica-alumina catalyst than was heretofore necessary for economical production of the desired polyamine products. The solid silica-alumina catalyst employed can be removed by simple filtration after water of reaction has been removed by simple flash distillation. The crude reaction product can be purified after separation from the silica-alumina by any of the conditional purification techniques, such as by distillation, to remove excess aniline. The resulting reaction product mixture of methylene-bridged polyphenylpolyamines or portions thereof can then be used directly as precursors for the preparation of the corresponding methylene-bridged polyphenylpolyisocyanates through the employment of any of the well-known phosgenation processes. The purified reaction product mixture of methylene-bridged polyphenylpolyamines can also be used as epoxy curing agents, urethane cross linkers, and the like as well known in the art.

DETAILED DESCRIPTION OF THE INVENTION

As mentioned hereinbefore, aniline-formaldehyde condensation reaction procedures heretofore employing solid acidic siliceous catalysts such as silica-alumina have required long reaction times and the employment of relatively large amounts of the solid catalyst, e.g. about 3 weight percent, basis aniline present. Most unexpectedly, I have discovered that the employment of oxalic acid in combination with silica-alumina as a co-catalyst system provides reduced condensation reaction times with the employment of much less silica-alumina than heretofore believed to be required. The employment of lesser amounts of silica-alumina in combination with the oxalic acid substantially eliminates the attendant difficulties of silica-alumina filtration during recovery of the desired methylene-bridged polyphenylpolyamine reaction product mixture. Moreover, surprisingly, it has been found that the employment of the combination of silica-alumina and oxalic acid as a co-catalyst system results in the production of methylene-bridged polyphenylpolyamine mixtures having increased 4,4'- isomer content in the methylene diphenylamine portion. Such results were unexpected inasmuch as silica-alumina catalyzed condensation reactions characteristically produce polyamine mixtures having diamine portions which contain relatively lower 4,4'- and higher 2,2'- and 2,4'- isomer contents than most other conventional procedures.

This inventor is not aware of any prior art disclosing the utilzation of oxalic acid or of a combination oxalic acid and silica-alumina as a co-catalyst system for the condensation reaction of a primary amine, such as aniline, with formaldehyde in the preparation of aromatic polyamines. U.S. Pat. No. 3,496,229, noted hereinbefore, teaches a process for the preparation of polyamines by the condensation reaction of an aromatic amine and formaldehyde wherein a low level synergistic catalyst system is employed consisting of at least 0.01 weight percent of a neutral salt and an acid having a pKa of at least 1.5 to 5 at 25°C. in water. Oxalic acid has a pKa of 1.23 (25°C. in water). Moreover, the process of this invention does not require the inclusion of a neutral salt in combination with the oxalic acid. Yet, most unexpectedly, there is no necessity to neutralize the crude condensation reaction product mixture to obtain the desired polymethylene polyphenylpolyamine product mixture.

The process of the invention is preferably carried out by mixing and reacting aniline and formaldehyde in the presence of from about 0.7 to about 1.75 weight percent silica-alumina and from about 0.25 to about 1.5 weight percent oxalic acid, each respectively based upon the weight of aniline charged. Any commercially available silica-alumina cracking catalyst can be employed. These catalysts are usually manufactured to contain about 5 to about 30 percent alumina and, as mentioned hereinbefore, are usually employed in solid powdered form, either supported or non-supported on an inert carrier material. The oxalic acid can also be employed in any of its commercially available forms. Specific amounts of silica-alumina and oxalic acid employed within the above described operational and preferred ranges have not been found to be critical and optimum amounts of each for a given condensation reaction can be readily determined by one having ordinary skill in the art without undue experimentation. However, experiments have shown that excessive amounts of oxalic acid result in reaction products with lowered amine content and, as expected, excessive amounts of silica-alumina are very difficult to filter. Thus the co-catalyst system of the invention should be employed in an amount of no more than about 3 weight percent, basis aniline charged, and preferably between about 0.6 weight percent to 3.0 weight percent. It can be readily understood that optimal amounts for a given reaction are dependent upon many processing variables that can be readily controlled as desired, e.g. the molar ratio of formaldehyde to aniline, specific temperatures and pressures, desired reaction times, the type of formaldehyde, and the like.

The molar ratio of aniline to formaldehyde employed may be varied within comparative wide limits. Thus, for example, from about 1 to about 10 moles of aniline may be employed per mole of formaldehyde. As known, at the lower aniline:formaldehyde molar ratios, such as ratios of from about 1:1 to about 2.5:1, the higher functionality, higher molecular weight polymethylene polyphenylpolyamines (triamines, tetramines, etc.) will be formed preferentially and the yield of higher polymers is approximately equal to or in excess of the yield of the diamine portion, methylene diphenylamine. However, as progressively larger amounts of aniline are used, the yield of the diamine portion is progressively increased at the expense of higher polymer yield. Thus, with aniline to formaldehyde molar ratios of from about 3:1 to about 10:1, the reaction product will be composed primarily of the diamine.

In carrying out the process of the invention, formaldehyde may be employed in any of its commercially available forms. Thus, formalin, paraformaldehyde, "stablized" methanol solutions of formaldehyde, etc.

may be employed interchangeably without adversely affecting the process.

Moreover, the inventive process can be carried out in accordance with any technique known in the art so as to provide intimate admixture of the aniline and formaldehyde and intimate contact thereof with the silica-alumina and oxalic acid co-catalyst system at elevated temperatures in liquid phase. For example, the oxalic acid can initially be mixed with the formaldehyde, preferrably employed in its commercially available "stabilized" methanol solution form, and admixed with aniline in conventional batch or continuous reactor systems containing the finely powdered solid silica-alumina.

The reaction may also be conducted in the presence or the absence of a solvent. When a solvent is employed, it may be any of the conventionally known hydrocarbon solvents or chlorinated hydrocarbons, such as aromatic or aliphatic solvents boiling within the range of from about 100° to about 250°C. The solvents should be employed in an amount sufficient to provide a single phase solution of the amine reaction product.

The reaction conditions for the inventive process preferably include a temperature within the range of from about 175° to about 210°C. under a pressure sufficient to maintain the reaction in liquid phase, e.g. usually within the range of from about atmospheric to about 300 psig. It is especially preferred to carry out the reaction of the process under autogenous pressure in a sealed reactor previously purged with an inert gas, such as nitrogen.

The reaction proceeds smoothly under the aforementioned conditions and is usually complete in a time period of about 1 to about 3 hours utilizing conventional equipment. Inasmuch as the formaldehydeaniline condensation reaction is exothermic, it is preferred to add formaldehyde at a rate such that the temperature of the reaction can be maintained.

Although, as mentioned hereinbefore, the specific amounts of silica-alumina and oxalic acid employed as a co-catalyst system in the present inventive process have not been found to be particularly critical within the above-described operational and preferred ranges, where it is desirable to utilize the methylene-bridged polyphenylpolyamine reaction product mixture as a precursor or feedstock for the preparation of a corresponding methylene-bridged polyphenylpolyisocyanate mixture, certain precautions should be observed. Experiments have shown that when aniline to formaldehyde molar ratios of less than about 3:1 and more than about 1.5 weight percent oxalic acid, basis aniline, are employed in the process of the invention and the product polyphenylpolyamine is subjected to conventional phosgenation techniques, the resultant corresponding isocyanate product generally has a viscosity higher than usually desired. These difficulties can be overcome by either employing aniline to formaldehyde molar ratios of above about 3:1 moles aniline:moles formaldehyde, e.g. above about 3:1 to about 10:1, or employing less than about 1.5 weight percent oxalic acid, basis aniline, or a combination of both. The amount of silica-alumina has not been found to adversely affect viscosity of the corresponding isocyanate product. Accordingly, where it is desirable to prepare corresponding polymethylene polyphenylpolyisocyanate mixtures it is especially preferred to carry out the process of the invention employing aniline to formaldehyde molar ratios of about 2.5:1 to about 3:1, about 0.25 to about 0.75, optimally about 0.35 to about 0.55, weight percent oxalic acid and about 0.7 to about 1.75 weight percent silica-alumina, basis aniline. Moreover, when these amounts of materials are employed, it is especially preferred to utilize reaction conditions of about 190° to about 210°C. elevated temperature under autogenous pressure, such as by carrying out the reaction in a sealed environment.

The reaction product mixture of methylene-bridged polyphenylpolyamines can be recovered from the resulting crude condensation reaction mixture very easily by the employment of conventional techniques. For example, it is preferred to initially strip water, and impurities such as methanol (if present) from the crude reaction product mixture such as by flash distillation. The solid silica alumina can then be readily filtered therefrom. The excess aniline is then removed by flash distillation. These techniques are well known to those skilled in the art and will not be described herein in detail. One of the primary advantages of the present invention is that the crude condensation reaction product can be easily filtered to remove the alumina-silica catalyst. Another primary advantage of the present invention is the fact that there is no requirement for filtering the crude condensation reaction product to remove any oxalic acid co-catalyst, if any be present, especially when the mixture is to be subsequently employed in conventional phosgenation processing for the preparation of corresponding methylene-bridged polyphenylpolyisocyanates.

In accordance with the present invention, the recovered mixture of methylene-bridged polyphenylpolyamines unexpectedly contains an increased 4,4'-isomer content in the methylene diphenylamine portion relative to a similar reaction product obtained using silica-alumina catalyst alone. Such polyphenylpolyamine mixtures have been found to be particularly useful as precursors of corresponding polyphenylpolyisocyanate mixtures prepared by any conventional phosgenation technique. These phosgenation techniques are well known in the art and amply described in the literature. Therefore a detailed discussion of such techniques will not be set forth herein.

The invention will be further illustrated by the following specific examples which are given by way of illustration and not as limitations.

EXAMPLE 1

To a 1 liter, stainless steel autoclave were charged 372 g. of aniline (4.0 moles), 150 ml. formalin (37% aqueous formaldehyde solution "stabilized" in 13–14 weight percent methanol; 2.0 moles formaldehyde), 5.6 g. powdered silica-alumina (1.5 weight %, basis aniline) and 5.6 g. oxalic acid dihydrate (1.5 weight %, basis aniline). The autoclave was purged with nitrogen, sealed and heated to 200°C. and maintained at that temperature for 2 hours. After cooling, the crude reaction mixture was stripped of water using a rotary evaporator, a 90°C. water bath and aspirator vacuum. The resulting anhydrous slurry was then filtered to remove the silica-alumina and stripped of aniline using a one plate distillilation head operated by taking the pot temperature to 200°C. at about 1 mm. Hg absolute pressure. The recovered reaction product mixture was analyzed and was found to contain no secondary amine by NMR (nuclear magnetic resonance) and 49 weight % diamine (diaminodiphenylmethane) by GLC (gas liquid chromotography) and GPC (gel permeation chromotography). Analysis further showed that the 4,4'-isomer content of the diamine portion (4,4'-diaminodiphenylmethane) was 77.6 weight %, basis total diaminodiphenylmethane present.

EXAMPLE II

The procedure of Example I was repeated using the same equipment, reaction conditions and amounts of aniline and formaldehyde, except that the catalyst consisted of 11.2 g. silica alumina (3.0 weight %, basis aniline) and no oxilac acid. The reaction mixture was stripped of water, filtered and stripped of aniline as described in Example I. Analysis of the resulting product mixture showed it contained no secondary amine (NMR) and 51 weight % diamine (diaminodiphenylmethane) by GLC and GPC. Analysis also showed that the 4,4'-isomer content of the diamine portion was 67.5 weight %, basis total diaminodiphenylmethane present.

EXAMPLE III

Example II was repeated using the identical reactants, reaction conditions and reaction equipment except that the catalyst consisted of only 5.6 grams silica-alumina catalyst (1.5 weight % basis aniline charged). Analysis of the anhydrous, filtered aniline-stripped reaction product showed it contained no secondary amine (NMR) and 49 weight % diaminodiphenylmethane by GPC (47 weight % by GLC) and the 4,4'-isomer content of the diamine portion was 66.0 weight %, basis total diaminodiphenylmethane present.

A comparison of the results of Example I to those of Examples II and III illustrate the increased 4,4'-isomer content of the diamine portion of a methylene-bridged polyphenylpolyamine reaction product mixture prepared in accordance with the present invention (Example I 77.6 weight percent) as compared to that produced by conventional processing (Example II, 67.5 weight percent) and to that prepared employing the same amount of silica-alumina catalyst in the absence of oxalic acid (Example III, 66.0 weight percent). Moreover, the anhydrous reaction product slurry of Example I was filtered substantially entriely free of silica-alumina much more easily than those of Examples II and III.

EXAMPLE IV

The procedure describd in Example I was repeated using the same reaction equipment, reaction conditions and quantities of reactants, except that 6.15 g. silica alumina (1.65 weight %, basis aniline) and 2.05 g. oxalic acid (0.55 weight %, basis aniline) were used as the catalyst system. Analysis of the resultant anhydrous, filtered aniline-stripped polyamine product showed it contained no secondary amine (NMR), 50–51.6 weight % diaminodiphenylmethane (diamine portion, by GLC and GPC) and 74.4 weight % 4,4'-isomer content in the diamine portion, basis total diamine present in the polyamine product. The results of this example illustrate that the use of only a small quantity of oxalic acid with the silica-alumina as a co-catalyst system produces increased 4,4'- isomer content in the diamine portion of the methylene-bridged polyphenylpolyamine mixture, prepared in accordance with the present invention. Filtration of the anhydrous slurry of this example also was much easier than filtration of the slurries of Examples II and III.

The foregoing disclosure and description of the invention are illustrative and explanatory and, obviously, many modifications and variations may be made without departing from the spirit and scope thereof. Therefore, only such limitations as are indicated in the following claims should be imposed.

I claim:

1. An improved process for the preparation of a mixture of methylene-bridged polyphenylpolyamines containing diaminodiphenylmethane having a high 4,4'-isomer content and higher molecular weight, higher functionality polymethylene polyphenylpolyamines by the catalyzed condensation reaction of aniline and formaldehyde, comprising the steps of:

mixing and reacting aniline and formaldehyde in the presence of up to about 3.0 weight percent of a co-catalyst system comprising about 0.1 to less than about 3.0 weight percent silica-alumina and about 0.1 to less than about 3.0 weight percent oxalic acid, based upon the weight of aniline present, at a temperture of about 150° to about 250°C. and a pressure of from about atmospheric to about 300 psig; and recovering the reaction product mixture of methylene-bridged polyphenylpolyamines.

2. A process in accordance with claim 1 wherein the aniline and formaldehyde are mixed and reacted in the presence of from about 0.7 to about 1.75 weight percent silica-alumina, based upon the weight of aniline present.

3. The process in accordance with claim 1 wherein the aniline and formaldehyde are mixed and reacted in the presence of from about 0.25 to about 1.5 weight percent oxalic acid, based upon the weight of aniline present.

4. The process in accordance with claim 1 wherein the aniline and formaldehyde are mixed and reacted in the presence of from about 0.7 to about 1.75 weight percent silica-alumina and from about 0.25 to about 1.75 weight percent oxalic acid, each being based upon the weight of aniline present.

5. The process in accordance with claim 1 wherein the oxalic acid is present in an amount of from about 0.25 to about 0.75 weight percent, based upon the weight of aniline present.

6. The process in accordance with claim 1 wherein the reaction product mixture of methylene-bridged polyphenylpolyamines is recovered by filtration to remove the silica-alumina catalyst therefrom.

7. The process in accordance with claim 1 wherein the aniline and formaldehyde are mixed and reacted to molar ratios of from about 1:1 to about 3:1 moles aniline:moles formaldehyde.

8. The process in accordance with claim 7 wherein the aniline and formaldehyde are mixed and reacted in the presence of from about 0.7 to about 1.75 weight percent silica-alumina and from about 0.25 to about 1.5 weight percent oxalic acid, each being based upon the weight of aniline present.

9. The process in accordance with claim 8 wherein said aniline and formaldehyde are mixed and reacted in the presence of from about 0.25 to about 0.75 weight percent oxalic acid, based upon the weight of aniline present.

10. The process in accordance with claim 7 wherein said reaction product mixture of methylene-bridged polyphenylpolyamines is recovered by filtration to remove the silica-alumina catalyst therefrom.

* * * * *